US010792415B2

(12) United States Patent
Roxas

(10) Patent No.: US 10,792,415 B2
(45) Date of Patent: Oct. 6, 2020

(54) FAILSAFE SYSTEM AND METHOD FOR A MEDICAL FLUID PROCEDURE

(71) Applicant: Fenwal, Inc., Lake Zurich, IL (US)

(72) Inventor: James Darren Roxas, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 119 days.

(21) Appl. No.: 16/008,391

(22) Filed: Jun. 14, 2018

(65) Prior Publication Data
US 2018/0361054 A1 Dec. 20, 2018

Related U.S. Application Data

(60) Provisional application No. 62/519,276, filed on Jun. 14, 2017.

(51) Int. Cl.
A61M 1/36 (2006.01)
A61M 1/34 (2006.01)
(Continued)

(52) U.S. Cl.
CPC ............ A61M 1/3696 (2014.02); A61M 1/02 (2013.01); A61M 1/0272 (2013.01); A61M 1/14 (2013.01); A61M 1/1601 (2014.02); A61M 1/1692 (2013.01); A61M 1/3496 (2013.01); A61M 1/367 (2013.01); A61M 1/3646 (2014.02); A61M 1/38 (2013.01); A61M 1/0209 (2013.01); A61M 1/3635 (2014.02); A61M 1/3672 (2013.01); A61M 2039/282 (2013.01); A61M 2202/0415 (2013.01); A61M 2202/0429 (2013.01); A61M 2202/0439 (2013.01);
(Continued)

(58) Field of Classification Search
None
See application file for complete search history.

(56) References Cited

U.S. PATENT DOCUMENTS 5,868,696 A    2/1999   Giesler et al.
6,419,822 B2   7/2002   Muller et al.
(Continued)

FOREIGN PATENT DOCUMENTS

CN       102003553 A        4/2011
WO      2014039086 A1       3/2014
WO    WO-2017048673 A1 *    3/2017  .......... A61M 1/0209

OTHER PUBLICATIONS

Extended European Search Report from the European Patent Office for Application No. 18174578.7-1115, dated Oct. 25, 2018.

Primary Examiner — Krishnan S Menon
(74) Attorney, Agent, or Firm — Cook Alex Ltd.

(57) ABSTRACT

A failsafe system for a medical fluid procedure, comprising a medical fluid processing apparatus comprising a sealer and a programmable controller driven by software, wherein the programmable controller is programmed to recognize a failure event from input from hardware components of the medical fluid processing apparatus. The system also comprises a disposable fluid circuit configured to associate with the medical fluid processing apparatus and comprising a tubing segment configured to fit within the sealer. The programmable controller is configured to seal the tubing segment by activating the sealer surrounding the tubing segment in response to an occurrence of the failure event.

21 Claims, 2 Drawing Sheets

(51) Int. Cl.
     *A61M 1/38*       (2006.01)
     *A61M 1/02*       (2006.01)
     *A61M 1/14*       (2006.01)
     *A61M 1/16*       (2006.01)
     *A61M 39/28*      (2006.01)

(52) U.S. Cl.
     CPC ..... *A61M 2205/14* (2013.01); *A61M 2205/15* (2013.01); *A61M 2205/276* (2013.01); *A61M 2205/60* (2013.01); *A61M 2205/6072* (2013.01); *A61M 2205/7554* (2013.01)

(56) References Cited

U.S. PATENT DOCUMENTS

| | | |
|---|---|---|
| 6,685,831 B2 | 2/2004 | Donig et al. |
| 2005/0049539 A1* | 3/2005 | O'Hara, Jr. ......... A61M 1/3686 604/4.01 |
| 2008/0234620 A1 | 9/2008 | Tonelli et al. |
| 2011/0118694 A1* | 5/2011 | Yodfat .................. G06F 19/00 604/500 |
| 2011/0294641 A1 | 12/2011 | Dolecek et al. |
| 2013/0320249 A1 | 12/2013 | Kim et al. |
| 2014/0053836 A1 | 2/2014 | Bathe et al. |
| 2016/0082185 A1 | 3/2016 | Grannell et al. |

\* cited by examiner

FAILSAFE SYSTEM AND METHOD FOR A MEDICAL FLUID PROCEDURE

CROSS-REFERENCE TO RELATED APPLICATIONS

This application claims the benefit of U.S. Provisional Patent App. No. 62/519,276 filed Jun. 14, 2017, which is expressly incorporated herein by reference in its entirety.

FIELD OF THE DISCLOSURE

The present disclosure relates generally to a failsafe mechanism for a medical device and, in particular to a failsafe system and method for a medical fluid procedure comprising a fluid circuit.

BACKGROUND

A variety of available blood processing systems allows for the collection and processing of particular blood components, rather than whole blood, from donors or patients. In the case of a blood donor, whole blood is drawn from the donor, a desired blood constituent isolated and collected, and the remaining blood components returned to the donor. By removing only particular constituents rather than whole blood, it takes the donor's body a shorter time period to recover to normal blood levels, thereby increasing the frequency with which the donor may donate blood. It is beneficial to increase in this manner the overall supply of blood constituents made available for health care, such as red blood cells (RBCs), leukocytes, plasma, and/or platelets, etc.

The separation phase of blood components from whole blood may be achieved through a spinning membrane or centrifugation, in which whole blood is passed through a centrifuge or membrane after it is withdrawn from the patient/donor. To avoid contamination and possible infection of the patient/donor, the blood is preferably contained within a sealed, sterile fluid flow system during the entire separation process. Typical blood processing systems thus may include a permanent, reusable hardware assembly containing the hardware (drive system, pumps, valve actuators, programmable controller, and the like) that pumps the blood, and a disposable, sealed and sterile fluid circuit that is mounted in cooperation on the hardware. In the case of separation via centrifugation, the hardware assembly includes a centrifuge that may engage and spin a separation chamber of the disposable fluid circuit during a blood separation step. The blood, however, may make actual contact only with the fluid circuit, which assembly may be used only once and then discarded. In the case of separation via a spinning membrane, a disposable single-use spinning membrane may be used in cooperation with the hardware assembly and disposable fluid circuit.

In the case of separation via centrifugation, as the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit.

In the case of separation via a spinning membrane, whole blood may be spun within a disposable spinning membrane, rather than within a separation chamber of a fluid circuit. Larger molecules, such as red blood cells, may be retained within one side of the membrane, while the smaller molecules, such as plasma, may escape through the pores of the membrane to the other side of the membrane. Various ones of these components can be selectively removed from the whole blood by forming appropriately located outlet ports in the housing of the membrane column. Various types of columns with different pore sizes may be used, depending on the components to be separated.

SUMMARY

According to an exemplary embodiment, the present disclosure is directed to a failsafe system for a medical fluid procedure, comprising a medical fluid processing apparatus comprising a sealer and a programmable controller driven by software, wherein the programmable controller is programmed to recognize a failure event from input from hardware components of the medical fluid processing apparatus. The system also comprises a disposable fluid circuit configured to associate with the medical fluid processing apparatus and comprising a tubing segment configured to fit within the sealer. The programmable controller is configured to seal the tubing segment by activating the sealer surrounding the tubing segment in response to an occurrence of the failure event.

According to an exemplary embodiment, the present disclosure is directed to a failsafe method for a medical fluid procedure, comprising providing a medical fluid processing apparatus comprising a sealer and a programmable controller driven by software, wherein the programmable controller is programmed to recognize a failure event from input from hardware components of the medical fluid processing apparatus. The method also comprises providing a disposable fluid circuit configured to associate with the medical fluid processing apparatus and comprising a tubing segment configured to fit within the sealer and activating the sealer and sealing the tubing segment via the programmable controller in response to an occurrence of the failure event.

According to an exemplary embodiment, the present disclosure is directed to a failsafe system for a medical fluid procedure, comprising a medical fluid processing apparatus comprising at least one of an apheresis machine, a dialysis machine, a device configured to administer a medicament, and an infusion device, comprising a radio frequency sealer in communication with a reader and a programmable controller driven by software, wherein the programmable controller is programmed to recognize from input from hardware components of the medical fluid processing apparatus a failure event comprising at least one of a leakage in a component of the fluid circuit, abnormal hematocrit, low blood volume, procedure pause event, procedure termination event, and failure to detect an authentication mark. The system also comprises a disposable fluid circuit configured to associate with the medical fluid processing apparatus and comprising a tubing segment incorporating an authentication mark recognizable by the reader and configured to fit within the radio frequency sealer, wherein the tubing segment is disposed between a first and second interference comprising at least one of a y-connection, port, clamp, pump raceway, valve, and pressure sensor when the disposable fluid circuit is in association with the medical fluid processing apparatus, wherein the first and second interferences are disposed at a distance of 2.0 in. or less with respect to each other along the tubing segment. The programmable controller is configured to proceed with the medical fluid procedure only when the tubing segment is detected within the radio frequency sealer and seal the tubing segment by activating the radio frequency sealer surrounding the tubing segment in response to an occurrence of the failure event.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may prevent use of a faulty disposable component of a disposable set by rendering the faulty component and/or other component of the disposable set unusable.

Some embodiments may prevent use of a counterfeit disposable component of a disposable set by rendering the counterfeit component of the set and/or other component of the set unusable.

There have been continuing efforts to automate the apparatus and systems used in the post-collection processing of whole blood, and an automated blood component separator for such post-collection processing may be employed. One class of such automated separators employs relatively rotating surfaces, at least one of which carries a porous membrane. An example of such a membrane separator is disclosed in PCT Patent Application Publication No. WO 2014/039086 A1, which is incorporated by reference in its entirety, although any suitable membrane separator may be used. Another class employs a centrifuge that utilizes centrifugal separation principles. An exemplary centrifugal separator is disclosed in U.S. Pat. No. 5,868,696, which is incorporated by reference in its entirety, although any suitable centrifugal separator may be used.

Both membrane separation and centrifugal separation systems may involve a durable processing system or device used in combination with a disposable processing set or circuit. The durable processing system may include a pump assembly that interacts with one or more of the components of the disposable circuit to draw blood or other bodily fluid from a blood source and move the blood or bodily fluid to another location within the disposable circuit by moving fluid through a fluid flow path.

Figure 1:
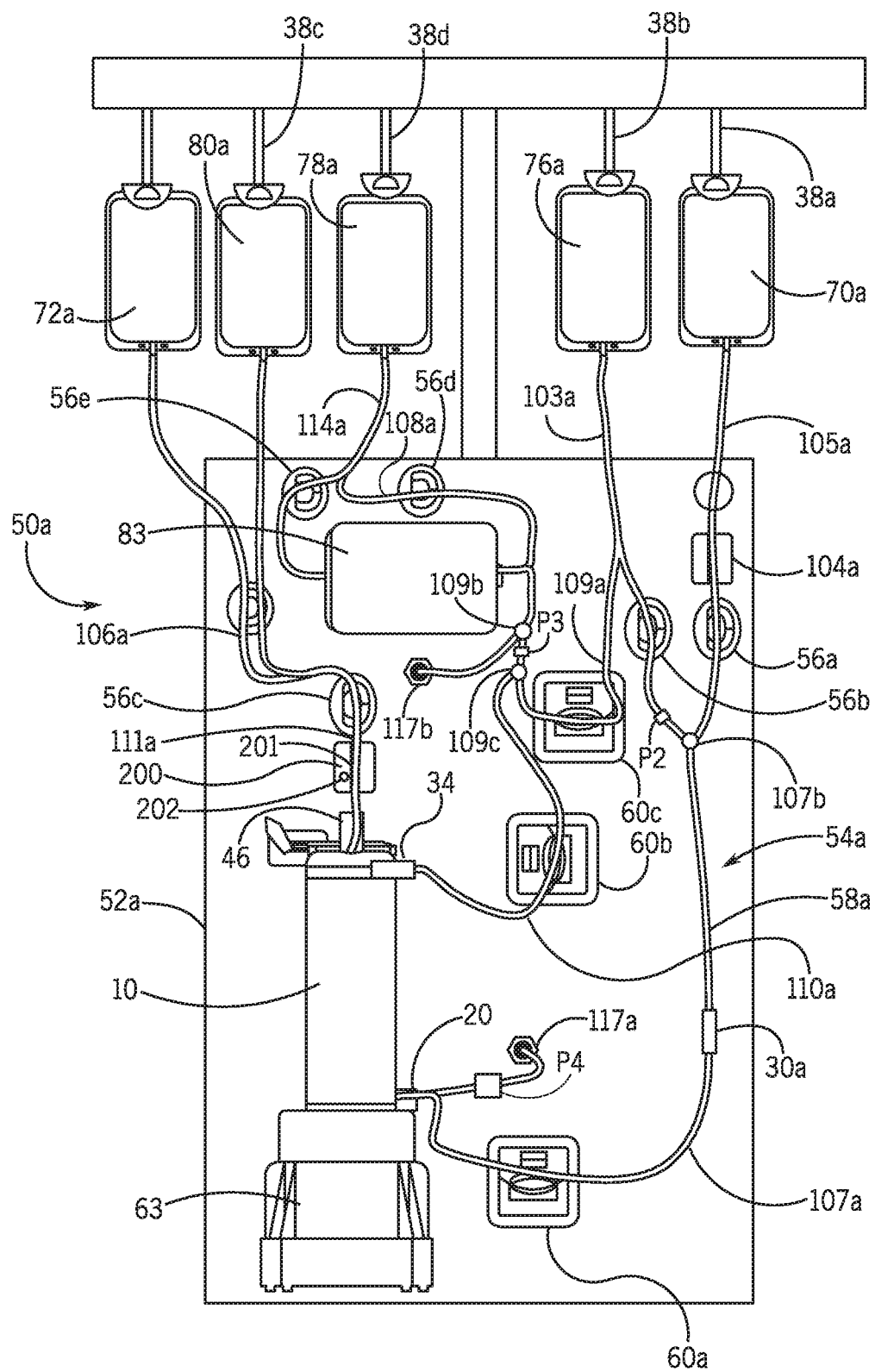
FIG. 1 depicts a fluid processing system in association with a disposable circuit, according to an exemplary embodiment.

FIG. 1 depicts a fluid processing system, generally at 50a, which includes a durable reusable processing device 52a and a disposable fluid flow circuit 54a for processing collected whole blood. The illustrated blood processing device 52a includes associated pumps, valves, sensors, displays and other apparatus for configuring and controlling flow of blood and additive solution through the disposable circuit. The device and the processing may be directed by an internal controller that includes a programmable microprocessor automatically controlling the operation of the pumps, valves, sensors, etc.

The processing device 50a may include, for example, a user input and output interface, e.g., touch screen (not illustrated), a pump station including a whole blood pump 60a, an RBC pump 60b and an additive solution pump 60c, blood separator mounting station and drive unit 63, tubing clamps/valves 56a-e, sterile connection or docking device 30a, and hematocrit sensor 104a. The processing device may also include hangers 38a-d, each associated with a weight scale, for suspending the various containers of the disposable fluid circuit.

The fluid flow circuit 54a may include an additive solution container 76a and associated fluid flow tubing 103a for withdrawing the additive solution, a whole blood source 70a (e.g., donor, patient, blood container) and associated fluid flow tubing 105a for withdrawal of collected whole blood from the container, and a processing module that may include a separator 10 (e.g., spinning membrane separator, separation chamber placed within a centrifuge), red blood cell (RBC) container 78a, plasma container 80a, and associated connecting tubing. In an embodiment in which a cassette is incorporated for organization of various fluid pathways, a pump cassette (not illustrated) may route the fluid flow through tubing loops that extend from the cassette, and each loop may be uniquely positioned to engage a particular one of the pumps 60a-c. The tubing may extend through the cassette or the cassette may have pre-formed fluid flow paths that direct the fluid flow. An exemplary cassette is described in U.S. the aforementioned U.S. Pat. No. 5,868,696.

Flow control valves 56a-e may assist in controlling flow through flexible plastic tubing 58a of the fluid flow circuit 54a. Each valve 56 may include a pair of clamping or pinching jaws, between which fluid flow tubing 58a of the fluid flow circuit 54a may be placed when the flow circuit 54a is assembled onto the face of the processing device 52a. The valves 56 may close or open the tubing in response to commands from the operating control system of the device 52a based on the particular process selected by the user. Typically the control system for device 52a may employ a programmable microprocessor-based controller that allows the device to be configured for one or more of different selected procedures for processing blood.

Turning to the disposable fluid flow circuit 54a, the preassembled circuit may be pre-sterilized and include the spinning membrane device 10, containers or bags 70a (e.g, containing blood to be processed), 72a (e.g., for receiving wash media), 76a (e.g., containing RBC additive solution), 78a (e.g., for receiving concentrated RBCs) and 80a (e.g., for receiving plasma), leukoreduction filter 83, and associated flexible tubing 58a connecting the various components in a fluid flow relationship.

In an embodiment in which blood source 70a is a blood storage container and not a donor/patient, container 70a may be any suitable container but is typically a flexible plastic pouch or bag in which approximately 450 ml of whole blood has been previously collected. The container 70a may be part of a separate system during collection and then joined to the rest of the fluid circuit 54a or actually part of the circuit 54a at the time of collection. At the time of collection, in accordance with customary procedure, the whole blood may be mixed with an anticoagulant located in the primary container to prevent premature coagulation. Accordingly, "whole blood" as used herein may include blood mixed with anticoagulant. Although the examples provided herein demonstrate whole blood as the blood to be processed, the blood to be processed, separated, and/or washed from the blood storage container 70a may be components other than whole blood, such as plasma, RBCs, white blood cells, or platelets.

Flexible plastic tubing 105a may be attached to the blood source 70a, such as by a sterile connection device, cannula, or other suitable attachment mechanism, and may define a whole blood fluid flow path between the blood source 70a and a junction with additive solution tubing 103a, which may extend from the additive solution container 76a to the flow path junction. The flow path junction between the whole blood flow path 105a and additive solution flow path 103a may be located upstream from inlet pump 60a. From the junction, the flow path may extend through tubing 107a to an inlet conduit 20 of the separator 10.

The separator 10 may have an exit orifice 34 that communicates with a retentate, e.g., concentrated cellular component, flow path tubing 110a for withdrawing retentate from the separator. The separator 10 may include a filtrate outlet orifice 46 that communicates with filtrate, e.g., plasma, flow path tubing 111a. A wash media tubing 106a may optionally branch out from the plasma flow path tubing 111a, such that the wash media tubing 106a and the plasma flow path tubing 111a lead respectively to wash media container 72a and plasma container 80a.

For reducing the number of leukocytes that may be present in the red cells in the event that concentrated RBCs are desired, the disposable fluid flow circuit 54a may optionally include a leukocyte reduction filter 83, which may be of any suitable construction for removing leukocytes from concentrated red cells without unduly causing hemolysis of red cells or reducing the number of red cells in the collected product. The concentrated red cells may then flow from the leukocyte reduction filter 83 through a RBC line 114a into RBC container 78a which may be of any suitable plastic material compatible with red cell storage. The flow circuit 54a may also include a bypass tubing 108a that directly communicates from cellular component flow path tubing 110a to RBC line 114a into RBC container 78a and bypass the leukocyte reduction filter 83. The flow circuit 54a may further include a tubing 109a that directly communicates from additive solution tubing 103a to bypass tubing 108a.

The durable processing device 52a may include a hematocrit sensor 104a for detecting the hematocrit of the whole blood flowing from the blood source 70a. The hematocrit detector 104a may be of any suitable design or construction, for example as described in U.S. Pat. No. 6,419,822, which is hereby incorporated by reference in its entirety.

The durable processing device 52a may also include control valves 56a and 56b, which may respectively be operated to control fluid from the blood source 70a and/or the additive solution container 76a. For controlling flow of blood into the separator, the processing device 52a may include an inlet pump 60a, which also may be of any suitable construction, and may be, for example, a peristaltic type pump which operates by progressive compression or squeezing of the tubing 107a forming the inlet flow path into the separator, a flexible diaphragm pump, or other suitable pump. A pressure sensor 117a may communicate with the inlet flow path 107a between the pump 60a and the spinning membrane device 10 to determine the inlet pumping pressure. The sensor 117a may output to a control system to provide an alarm function in the event of an over-pressure condition or an under-pressure condition or both.

To control the flow rate of the cellular component from the spinning membrane device 10, the durable processing device 52a may also include an outlet pump 60b that is associated with the cellular component flow path 110a, and functions in the manner similar to that described with respect to inlet pump 60a. It also may be of any suitable construction such as a peristaltic pump, a flexible diaphragm, or other suitable pumping structure. The plasma flow path 111a exiting the separator 10 may, rather than being controlled by a pump, be controlled by the volumetric flow rate through the plasma flow path tubing 111a. The volumetric flow rate is the difference between the inlet volumetric flow rate from pump 60a and the outlet volumetric flow rate from pump 60b. The processing device 52a may, however, include a clamp 56c for controlling flow of plasma through the plasma flow path tubing 111a.

The processing device 52a may also include an additive solution pump 60c that is associated with tubing 109a that connects additive solution tubing 103a to the bypass tubing 108a, and may function in a manner similar to that described with respect to inlet pump 60a and outlet pump 60b. The additive solution pump 60c may function to direct flow between the additive solution tubing 103a and the bypass tubing 108a or the cellular component flow path tubing 110a.

The flow circuit 54a may also include a plasma container 80a in fluid communication with the plasma flow path tubing 111a for receiving plasma separated by the separator 10. The plasma that is collected in container 80a may be largely cell free plasma and may be suitable for administration to patients, freezing for storage or subsequent processing.

In one embodiment, initial priming of the blood processing system 50a may be performed. Priming the system 50a may assist in wetting the membrane within the spinning membrane device 10 and removing air from the flow pathways. In one embodiment, additive solution from additive solution container 76a may be used to prime the system 50a, but fluids such as wash media and/or whole blood may also be used. Additive solutions that may be used include any suitable chloride or non-chloride solution, such as saline and/or any aqueous solution with an osmolality near that of blood.

During the system prime, pumps 60a, 60b, and 60c may all be operative to flow additive solution from the additive solution container 76a. Inlet pump 60a may pump fluid into the inlet conduit 20 of the spinning membrane device 10. The fluid may prime the device 10 and exit through the exit orifice 34, where the fluid may be pumped via pump 60b through the cellular component flow path tubing 110a, through the leukocyte reduction filter 83, through the RBC tubing 114a, and to the RBC container 78a. Simultaneously, pump 60c may pump fluid from the additive solution container 76a through tubing 109a directly to the leukocyte reduction filter 83. In conjunction with pumps 60a, 60b, and 60c, direction of fluid flow may be manipulated by a layout of open and closed valves 56.

Subsequent to priming the system 50a, separation of the initial blood composition to be processed may be performed. In an embodiment in which the initial blood composition to be processed is whole blood from the blood source 70a, the inlet pump 60a may pump the whole blood along inlet tubing 107a to the inlet conduit 20 of the spinning membrane device 10. Within the device 10, plasma may exit the device 10 through the plasma outlet orifice 46 into the plasma flow path tubing 111a. The plasma may then be channeled through tubing 111a into the plasma container 80a and diverted away from tubing 106a by clamping wash media tubing 106a. Within the device 10, cellular components may be pumped out of the exit orifice 34 by the outlet pump 60b into the cellular component flow path 110a. In the event that a RBC product substantially free of white blood cells (WBCs) and platelets are desired, the cellular components may be pumped via outlet pump 60b from the path 110a into the leukocyte reduction filter 83 by closing valve 56d and opening valve 56e. Prior to the cellular components entering the leukocyte reduction filter 83, additive solution pump 60c may pump additive solution from additive solution container 76a via tubing 109a into path 110a of the cellular components. Dilution of the cellular components with additive solution prior to entering the leukocyte reduction filter 83 may minimize clogging of the filter 83 and effectuate efficient filtration. A RBC product substantially free of WBCs and platelets may then leave the leukocyte reduction filter 83 through the RBC tubing 114a into the RBC container 78a.

Subsequent to collecting the desired blood component, additional recovery of the desired blood component may be performed. The inlet pump 60a may pump additive solution from the additive solution container 76a along additive solution tubing 103a through both inlet flow path 107a and tubing 109a. Additive solution from inlet flow path 107a may be pumped through inlet conduit 20 of the spinning membrane device 10 and recover residual cellular component remaining in the device 10. By closing control valve 56c, the additive solution and cellular component mixture may exit only through the exit orifice 34 and be pumped through cellular component flow path tubing 110a via outlet pump 60b. The additive solution in path 110a may enter the leukocyte reduction filter 83 and recover residual RBC product remaining in the filter 83. The additive solution and recovered RBC product may then be pumped through the RBC line 114a and into the RBC container 78a. Although the aforementioned fluid procedure comprises priming, separation, and recovery, it should be understood that a medical fluid procedure may comprise a different set of steps, such as those including multiple separation cycles, washing, drawing source fluid, and/or reinfusion.

During the performance of the various steps of a medical fluid procedure, the system 50a may have various failsafe mechanisms to prevent faulty procedures, alert a device operator of detected issues, and/or prevent use of unauthorized disposable components. A failsafe mechanism may be triggered by detection of failure events programmed into the system 50a. For example, a leakage in any of the components of the fluid circuit 58a may be detected by the system 50a, e.g., via one or more of the hematocrit sensor 104a, pressure sensors 117a, 117b, hangers 38a-d, etc. In another example, abnormal hematocrit and/or low patient/donor blood volume may be detected by, e.g., the hematocrit sensor 104a, hangers 38a-d, etc. In another example, any procedure pause/termination event (e.g., initiated by operator, automatically initiated, in response to an alarm, etc.) may be programmed as a failure event. In another example, attempts may be made to use counterfeit kits not suitable for the system 50a and/or not recognized by the system 50a. In such instances of failure events, system 50a may be configured to discontinue the procedure and render the disposable kit 54a not useable by sealing off a portion of the kit 54a and necessitating use of a new disposable kit.

A seal-off fail safe mechanism may be desirable in cases in which a failure event carries relatively high risk and/or is susceptible to improper override. For example, failure events such as disposable component leakages, abnormal hematocrit, abnormal fluid volume, pause events, termination events, and/or unrecognized disposable components may be programmed into the system 50a as a high risk failure event warranting activation of the seal-off mechanism. A failure event amenable to improper override may be a situation in which the system 50a may be fooled into recognizing that an adequate corrective action to the failure event has been made even when an adequate corrective action has not been made. For example, if the system 50a detects a leakage via its scales/hangers 38a-d while priming the fluid circuit 58a and triggers an alarm, without a fail-safe mechanism that renders the circuit 58a unusable, an operator may temporarily replace container(s) 70a, 76a, 78a, 80a on scale(s) 38a-d with container(s) from another fluid circuit to deactivate the alarm, and once the alarm is deactivated, return container(s) 80a, 78a, 76a, 70a that triggered the alarm to scale(s) 38a-d and resume a procedure that in actuality may still be faulty.

Turning to FIG. 1, a sealer 200 may be incorporated into the system 50a and be programmed to be activated in response to designated failure events. In one embodiment, sealer 200 may be a radio frequency (RF) sealer utilizing RF energy, although any suitable sealing mechanism may be used. An example of a RF sealing mechanism is disclosed in US Patent Publication No. 2013/0320249, which is incorporated by reference in its entirety, although any suitable sealer may be used. In one embodiment, the system 50a may be configured to commence or proceed with a fluid processing procedure only when a tubing segment 201 of the circuit 58a is detected within the seal-off radio frequency (RF) sealer 200. While described with reference to tubing used in an apheresis machine, the concepts described herein may be applied to other tubes and other forms of fluid systems. Other forms of fluid systems may include, but are not limited to, dialysis machines, medical devices configured to administer a medicament, infusion devices, and other medical devices configured to process a sample of a biological fluid.

The tubing segment 201 configured to fit within the sealer 200 may be formed of a relatively flexible material, such as PVC or silicone. In an embodiment in which authentication of circuit 58a or a component of circuit 58a is desired, tubing segment 201 may optionally include an authentication mark (e.g., hologram, watermark, barcode, image, chips, taggant, etc.) that can be read by one or more transponders or readers 202 included within the sealer 200, although any type of authentication system may be used. In one embodiment, a RF authentication system incorporating RF readers and RFID tags (active or passive) may be used.

In one embodiment, the sealer 200 may be strategically placed on the system 50a at locations along the fluid circuit 58a that, when mounted on the system 50a, are configured to have relatively short stretches of uninterrupted tubing. Uninterrupted tubing may be characterized as a continuous length of tubing comprising no interferences such as a y-connection, port of a container or separator, clamp, pump raceway, pressure sensor, or any other entity that obstructs a continuous length of tubing. For example, in FIG. 1, filtrate flow path 111 comprises uninterrupted tubing at tubing segment 201, which stretches from filtrate outlet orifice 46 to tubing clamp/valve 56c. Likewise, point P2 along the circuit 58a between control valve 56b and y-connection 107b is another example of a location at which sealer 200 may be placed. Point P3 along the circuit 58a between y-connections 109b and 109c is another example of a location at which sealer 200 may be placed. Point P4 along the circuit 58*a* between inlet port 20 and pressure sensor 117*a* is another example of a location at which sealer 200 may be placed. Placing the sealer along relatively short stretches of uninterrupted tubing may help deter attempts to unseal, e.g., by using a tube welder such as sterile connection device 30*a*, a tubing segment that has been sealed by the sealer 200 in response to a failure event. Due to tube welders generally requiring longer stretches of uninterrupted tubing than required by tube sealing devices, placing the sealer 200 along short tubing segments may preclude attempts to unseal sealed segments.

Figure 2A:
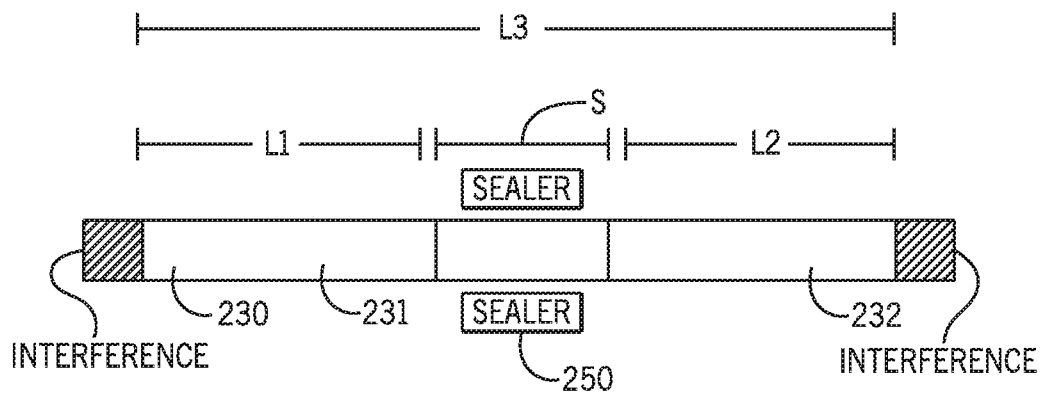
FIGS. 2A and 2B are lateral views of tubing segments disposed between a sealer and welder, respectively, according to an exemplary embodiment.
Figure 2B:
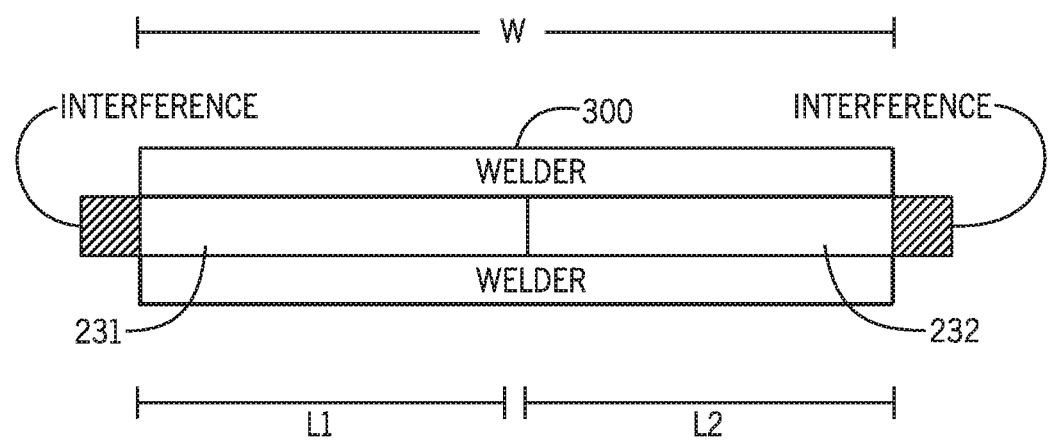

FIGS. 2A and 2B are lateral views of tubing segments disposed between a sealer (FIG. 2A) and welder (FIG. 2B) to illustrate differences in the amount of tubing clearance required. FIG. 2A shows uninterrupted tubing segment 230 comprising a total length L3. A sealer 250, when activated, may seal segment 230 along a length equal to S, leaving two segments 231 and 232 having respective lengths L1 and L2. The sum of lengths L1 and L2 minus length S is equal to total length L3. FIG. 2B shows segments 231 and 232 having respective lengths L1 and L2 in a sterile-welding device 300 requiring a clearance length W. Depending on the type of sterile-welding device, a total clearance length W may be required to sterile-connect, or each segment 231 or 232 may require a minimum clearance length, e.g., one half of W. A typical sterile-welding device may require a clearance length for each tubing segment to be welded of approximately 0.5 in. and above and more typically 1.0 in. and above, for a total clearance length W of 1.0 in. and above and more typically 2.0 in. and above. A typical sealing device may require a clearance length S in the range of 0.1 to 0.3 in. FIGS. 2A and 2B illustrate that when L1+L2<W, or when L1<½ W and L2<½ W, a tubing segment that has been sealed in response to a failure event may not be welded together easily.

Turning to the sealer 200 of FIG. 1 and alternative placement points P2, P3, and/or P4, attempts to unseal a tubing segment that has been sealed in response to a failure event may be effectively deterred by placing the sealer 200 along stretches of uninterrupted tubing 201 having a total length less than that of a typical sterile welding device. In one embodiment, tubing 201 may have a length of 2.0 in. or less. In another embodiment, tubing 201 may have a length in the range of 0.1 to 1.0 in. and preferably in the range of 0.3 to 2.0 in.

Without limiting the foregoing description, in accordance with one aspect of the subject matter herein, there is provided a failsafe system for a medical fluid procedure, comprising a medical fluid processing apparatus comprising a sealer and a programmable controller driven by software, wherein the programmable controller is programmed to recognize a failure event from input from hardware components of the medical fluid processing apparatus. The system also comprises a disposable fluid circuit configured to associate with the medical fluid processing apparatus and comprising a tubing segment configured to fit within the sealer. The programmable controller is configured to seal the tubing segment by activating the sealer surrounding the tubing segment in response to an occurrence of the failure event.

In accordance with a second aspect which may be used or combined with the immediately preceding aspect, the failure event comprises at least one of a leakage in a component of the fluid circuit, abnormal hematocrit, abnormal fluid volume, procedure pause event, procedure termination event, and failure to detect an authentication mark.

In accordance with a third aspect which may be used or combined with any of the preceding aspects, the hardware components comprise at least one of the sealer, a hematocrit sensor, a pressure sensor, and scale configured to detect the failure event.

In accordance with a fourth aspect which may be used or combined with any of the preceding aspects, the programmable controller is further configured to proceed with the medical fluid procedure only when the tubing segment is detected within the sealer.

In accordance with a fifth aspect which may be used or combined with any of the preceding aspects, the medical fluid processing apparatus comprises at least one of an apheresis machine, a dialysis machine, a medical device configured to administer a medicament, and an infusion device.

In accordance with a sixth aspect which may be used or combined with any of the preceding aspects, a reader is in communication with the sealer, and the tubing segment comprises an authentication mark recognizable by the reader in communication with the sealer.

In accordance with a seventh aspect which may be used or combined with any of the preceding aspects, the tubing segment is disposed between a first and second interference when the disposable fluid circuit is in association with the medical fluid processing apparatus.

In accordance with an eighth aspect which may be used or combined with the seventh aspect, the first and/or second interference comprises at least one of a y-connection, port, clamp, valve, pump raceway, and pressure sensor.

In accordance with a ninth aspect which may be used or combined with any of the seventh and eighth aspects, the first and second interferences are disposed at a distance of 2.0 in. or less with respect to each other along the tubing segment.

In accordance with a tenth aspect which may be used or combined with any of the seventh through ninth aspects, the first and second interferences are disposed at a distance in the range of 0.1 to 1.0 in. with respect to each other along the tubing segment.

In accordance with an eleventh aspect, there is provided a failsafe method for a medical fluid procedure, comprising providing a medical fluid processing apparatus comprising a sealer and a programmable controller driven by software, wherein the programmable controller is programmed to recognize a failure event from input from hardware components of the medical fluid processing apparatus. The method also comprises providing a disposable fluid circuit configured to associate with the medical fluid processing apparatus and comprising a tubing segment configured to fit within the sealer and activating the sealer and sealing the tubing segment via the programmable controller in response to an occurrence of the failure event.

In accordance with a twelfth aspect which may be used or combined with the eleventh aspect, the failure event comprises at least one of a leakage in a component of the fluid circuit, abnormal hematocrit, abnormal fluid volume, procedure pause event, procedure termination event, and failure to detect an authentication mark.

In accordance with a thirteenth aspect which may be used or combined with the eleventh and twelfth aspects, the hardware components comprise at least one of the sealer, a hematocrit sensor, a pressure sensor, and scale configured to detect the failure event.

In accordance with a fourteenth aspect which may be used or combined with any of the eleventh through thirteenth aspects, the medical fluid procedure proceeds only when the tubing segment is detected within the sealer.

In accordance with a fifteenth aspect which may be used or combined with any of the eleventh through fourteenth aspects, the medical fluid processing apparatus comprises at least one of an apheresis machine, a dialysis machine, a medical device configured to administer a medicament, and an infusion device.

In accordance with a sixteenth aspect which may be used or combined with any of the eleventh through fifteenth aspects, a reader is in communication with the sealer and is configured to recognize an authentication mark on the tubing segment. The tubing segment is sealed via the programmable controller if no authentication mark is recognizable by the reader.

In accordance with a seventeenth aspect which may be used or combined with any of the eleventh through sixteenth aspects, the tubing segment is disposed between a first and second interference when the disposable fluid circuit is in association with the medical fluid processing apparatus.

In accordance with an eighteenth aspect which may be used or combined with the seventeenth aspect, the first and/or second interference comprises at least one of a y-connection, port, clamp, valve, pump raceway, and pressure sensor.

In accordance with a nineteenth aspect which may be used or combined with any of the seventeenth and eighteenth aspects, the first and second interferences are disposed at a distance of 2.0 in. or less with respect to each other along the tubing segment.

In accordance with a twentieth aspect, there is provided a failsafe system for a medical fluid procedure, comprising a medical fluid processing apparatus comprising at least one of an apheresis machine, a dialysis machine, a device configured to administer a medicament, and an infusion device, comprising a radio frequency sealer in communication with a reader and a programmable controller driven by software, wherein the programmable controller is programmed to recognize from input from hardware components of the medical fluid processing apparatus a failure event comprising at least one of a leakage in a component of the fluid circuit, abnormal hematocrit, low blood volume, procedure pause event, procedure termination event, and failure to detect an authentication mark. The system also comprises a disposable fluid circuit configured to associate with the medical fluid processing apparatus and comprising a tubing segment incorporating an authentication mark recognizable by the reader and configured to fit within the radio frequency sealer, wherein the tubing segment is disposed between a first and second interference comprising at least one of a y-connection, port, clamp, pump raceway, valve, and pressure sensor when the disposable fluid circuit is in association with the medical fluid processing apparatus, wherein the first and second interferences are disposed at a distance of 2.0 in. or less with respect to each other along the tubing segment. The programmable controller is configured to proceed with the medical fluid procedure only when the tubing segment is detected within the radio frequency sealer and seal the tubing segment by activating the radio frequency sealer surrounding the tubing segment in response to an occurrence of the failure event.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A medical fluid processing apparatus, comprising:
   a sealer configured to receive at least a portion of a tubing segment of a fluid flow circuit, the sealer including an authentication system comprising one or more transponders included within the sealer and configured to authenticate the fluid flow circuit; and
   a controller configured to receive input from the authentication system and, upon receiving input from the authentication system indicative of a failure to authenticate the fluid flow circuit, activate the sealer to seal said at least a portion of the tubing segment received by the sealer, so as to render the fluid flow circuit unusable.

2. The medical fluid processing apparatus of claim 1, wherein the controller is further configured to receive input from at least one component of the medical fluid processing apparatus and, upon receiving input indicative of a failure event is selected from the group consisting of a leakage in a component of the fluid circuit, abnormal hematocrit, abnormal fluid volume, a procedure pause event, and a premature procedure termination event, activate the sealer to seal said at least a portion of the tubing segment received by the sealer, so as to render the fluid flow circuit unusable.

3. The medical fluid processing apparatus of claim 2, wherein said at least one component is selected from the group consisting of a hematocrit sensor, a pressure sensor, and a scale.

4. The medical fluid processing apparatus of claim 1, wherein the controller is further configured to proceed with a medical fluid procedure only when said at least a portion of the tubing segment is detected within the sealer.

5. The medical fluid processing apparatus of claim 1, configured as an apparatus selected from the group consisting of an apheresis machine, a dialysis machine, a medical device configured to administer a medicament, and an infusion device.

6. The medical fluid processing apparatus of claim 1, wherein the one or more transponders are configured to detect an authentication mark associated with said at least a portion of the tubing segment.

7. The medical fluid processing apparatus of claim 1, wherein the sealer is disposed between first and second interferences separated by a distance no greater than 2.0 inches.

8. The medical fluid processing apparatus of claim 7, wherein the first and/or second interference are each selected from a group consisting of a y-connection, a port, a clamp, a valve, a pump raceway, and a pressure sensor.

9. A failsafe method for a medical fluid procedure, comprising:
   providing a medical fluid processing apparatus comprising a sealer including an authentication system comprising one or more transponders included within the sealer;
   mounting a fluid flow circuit to the medical fluid processing apparatus, with at least a portion of a tubing segment of the fluid flow circuit received by the sealer;
   attempting to authenticate the fluid flow circuit using the authentication system; and
   activating the sealer to seal said at least a portion of the tubing segment in response to a failure of the authentication system to authenticate the fluid flow circuit, so as to render the fluid flow circuit unusable.

10. The failsafe method of claim 9, further comprising activating the sealer to seal said at least a portion of the tubing segment in response to a failure event selected from the group consisting of a leakage in the fluid flow circuit, abnormal hematocrit, abnormal fluid volume, a procedure pause event, and a premature procedure termination event.

11. The failsafe method of claim 10, wherein a signal indicative of the failure event is generated by at least one component of the medical fluid processing apparatus selected from the group consisting of a hematocrit sensor, a pressure sensor, and a scale.

12. The failsafe method of claim 9, further comprising proceeding with the medical fluid procedure only when said at least a portion of the tubing segment is detected within the sealer.

13. The failsafe method of claim 9, wherein the medical fluid procedure is selected from the group consisting of apheresis, dialysis, administration of a medicament, and infusion.

14. The failsafe method of claim 9, wherein said attempting to authenticate the fluid flow circuit using the authentication system includes attempting to detect an authentication mark associated with said at least a portion of the tubing segment.

15. The failsafe method of claim 9, wherein the sealer is disposed between first and second interferences separated by a distance no greater than 2.0 inches.

16. The failsafe method of claim 15, wherein the first and/or second interference is selected from the group consisting of a y-connection, a port, a clamp, a valve, a pump raceway, and a pressure sensor.

17. A failsafe system for a medical fluid procedure, comprising:
a disposable fluid flow circuit including a tubing segment; and
a medical fluid processing apparatus configured as an apparatus selected from the group consisting of an apheresis machine, a dialysis machine, a device configured to administer a medicament, and an infusion device, comprising
a radio frequency sealer receiving at least a portion of the tubing segment and including an authentication system comprising one or more transponders included within the radio frequency sealer, and
a controller configured to receive input from the authentication system, wherein
the radio frequency sealer is disposed between first and second interferences each selected from a group consisting of a y-connection, a port, a clamp, a pump raceway, a valve, and a pressure sensor and separated by a distance of 2.0 in. or less, and the controller is configured to
proceed with the medical fluid procedure only when said at least a portion of the tubing segment is detected within the radio frequency sealer, and
activate the radio frequency sealer to seal said at least a portion of the tubing segment in response to receipt of input from the authentication system indicative of a failure to authenticate the fluid flow circuit.

18. The medical fluid processing apparatus of claim 1, wherein the sealer is configured as a radio frequency sealer.

19. The failsafe method of claim 9, wherein the sealer is configured as a radio frequency sealer.

20. The medical fluid processing apparatus of claim 1, wherein the authentication system comprises an RF authentication system.

21. The failsafe method of claim 9, wherein the authentication system comprises an RF authentication system.

* * * * *